United States Patent

Kim et al.

[11] 3,999,554
[45] Dec. 28, 1976

[54] KIM'S NASOGASTRIC TUBE

[76] Inventors: Il Bong Kim; George Spector, both c/o George Spector, 3615 Woolworth Bldg., 233 Broadway, New York, N.Y. 10007

[22] Filed: Jan. 21, 1975

[21] Appl. No.: 542,835

[52] U.S. Cl. .................. 128/350 R; 128/240; 238/276
[51] Int. Cl.² ........................ A61M 27/00
[58] Field of Search .......... 128/240, 241, 276–278, 128/348, 349 R, 350 R, 351

[56] References Cited
UNITED STATES PATENTS

| | | | |
|---|---|---|---|
| 2,492,384 | 12/1949 | Kaslow | 128/350 R X |
| 2,508,690 | 5/1950 | Schmerl | 128/276 |
| 2,804,075 | 8/1957 | Borden | 128/277 |
| 3,114,373 | 12/1963 | Andersen | 128/276 X |
| 3,823,720 | 7/1974 | Tribble | 128/350 R |

*Primary Examiner*—Dalton L. Truluck

[57] ABSTRACT

An improved nasogastric tube in which a perforated irrigation tube is integrally formed with an infusion tube and a sump tube on its inner side, the irrigation tube being closed on one end that extends into a patient's stomach, the infusion tube extending a small distance through the closed end of the irrigation tube; the infusion tube delivering infusion into the stomach, the sump tube delivering air into the closed end of the irrigation tube, and the irrigation tube removing blood clots and the like from the stomach.

1 Claim, 5 Drawing Figures

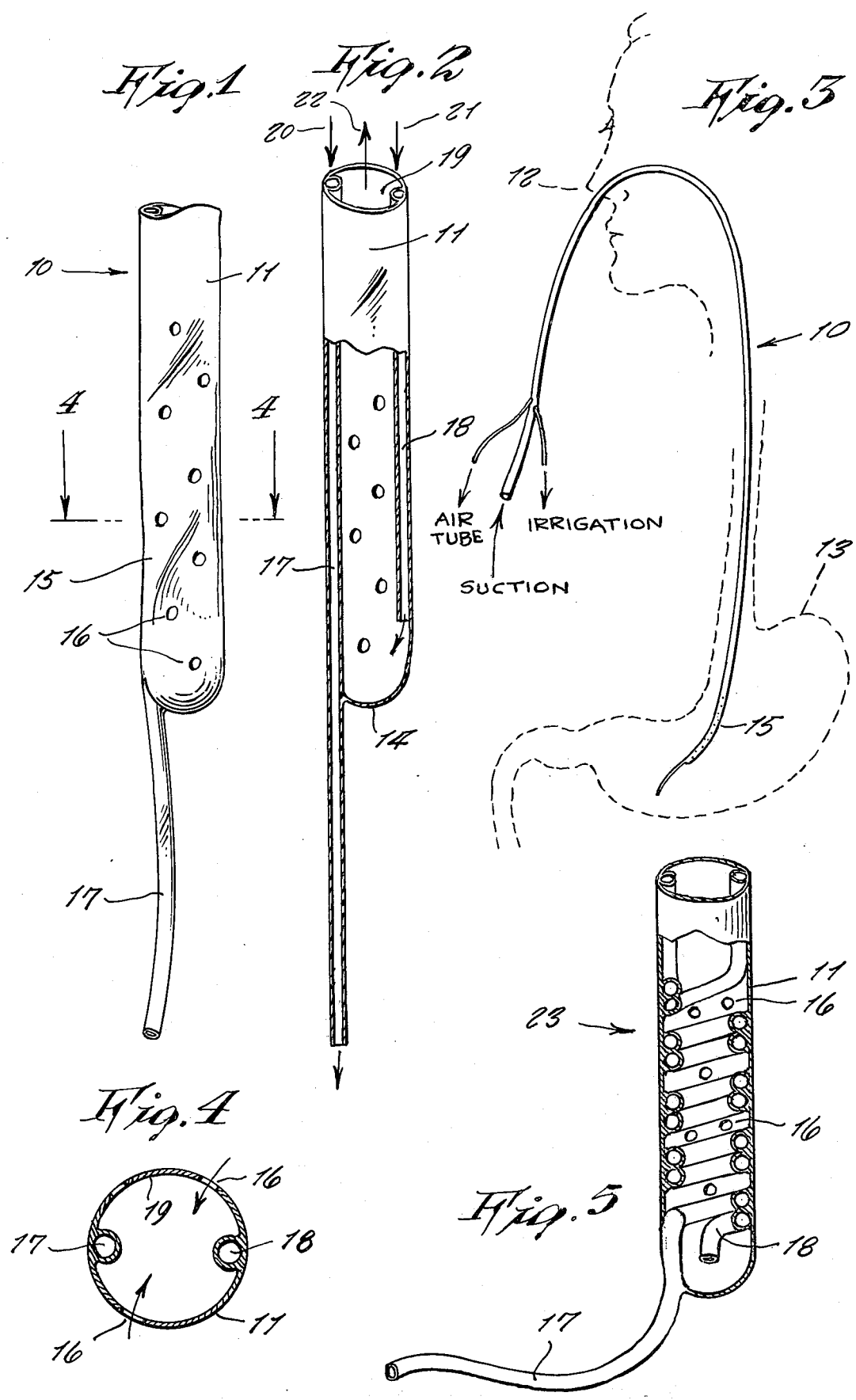

KIM'S NASOGASTRIC TUBE

This invention relates generally to therapeutic apparatus for treatment where massive bleeding occurs in a stomach or duodenum.

It is well known that in a patient having massive bleeding from the stomach or duodenum, a nasogastric tube is used for diagnostic and therapeutic purposes. The therapy comprises neutralization of gastric acidity by infusion of anti-acid mixture, and removal of blood clot from the stomach by suction via the tube.

In order to meet proper conservative treatment of the upper-gastro-intestinal bleeding, there are three types of management used at the present time:

Type I (Levin type N-G tubes). This can be used as a continuo us suction, intermittant suction, with intermittant infusion of the above mentioned fluid, shutting off the suction.

Type II (Two Levin type N-G tubes). Two tubes are inserted from the nostrils to the stomach and used as continuous infusion and suction.

Type III (Sump Type). Continuous infusion and suction, or only suction with or without intermittant suction.

Practically continuous infusion and suction is the most effective because the stomach content is washed out in this way continuously. For this reason, type I is not adequate, because two routes are required. Type II, practically considered, is very difficult in inserting two tubes, because when the second tube is inserted, the two tubes, made of a plastic material, rub against each other, and most of the time one fails to insert two tubes. What is even worse is that the patient feels more discomfort with two tubes being in the nostrils and esophagus. Type III has the tube used as infusion and a sump. However, when it is used as an infusion, the infusion hole is too close to the holes of suctioning, so that infused fluid is directed to the suction holes and is suctioned out immediately. Thus irrigation or dilution of the stomach content is not properly performed. However, if this tube were to be used as a sump, it would work out all right.

Accordingly, it is a principal object of the present invention to provide a new type IV (comprising a Kim's Nasogastric Tube) in which three lumens in one tube and an extra length of the tube at the tip of a main tube are provided so to overcome and eliminate the above described objectionable situations.

Another object is to provide a Kim's nasogastric tube in which an infusion tube extends beyond an end of a wider main tube; the infusion tube being flexible and of soft material so that it floats by motility of the stomach and it will distribute all the infusion fluid throughout the entire stomach cavity, so that in this way irrigation, neutralization and blood clot removal is better performed than above described.

Other objects are to provide a Kim's Nasogastric Tube which is simple in design, inexpensive to manufacture, durable in construction, easy to use and efficient in operation.

These and other objects will be readily evident upon a study of the following specification and the accompanying drawing wherein:

FIG. 1 is a side view of a lower end portion of the invention, shown enlarged.

FIG. 2 is a side cross sectional view thereof taken in a same plane as FIG. 1.

FIG. 3 is a side view of the invention shown in operative position within a stomach.

FIG. 4 is a further enlarged transverse cross sectional view taken on line 4—4 of FIG. 1.

FIG. 5 is a view similar to FIG. 2 showing a modification wherein the assembly includes infusion and air tubes in a spiral arrangement to reinforce the suction tube against collapsing.

Referring now to the drawings in detail, and more particularly to FIGS. 1 through 4 at this time, the reference numeral 10 represents a Kim's nasogastric tube according to the present invention wherein there is a main, or suction tube 11 of serial size 16, 18 or 20 French and length 50 inches, made of flexible plastic material and which is of sufficient length so it can be extended through a person's nostrels 12 down into the stomach 13, which the external end is connectable to a suitable vacuum source. The inner end of the tube 11 is rounded and closed by an end wall 14. The entire length of a terminal portion 15 of the tube 11 which fits into the stomach is perforated with small openings 16.

Upon diametrically opposite inner sides of the tube 11 a pair of smaller diameter tubes 17 and 18 are integrally formed with the tube 11 side wall 19, and are accordingly of a same material as tube 11. The tube 17 additionally protrudes through the end wall 14 of tube 11 for about two to two and one half inches; the opposite ends of the tube being open, and serving as an infusion tube. The tube 18 terminates within the interior of tube 11 relatively near the end wall 14, and serves as a sump tube. The both tubes extend the full length of the tube 11 except near the other end of tube 11, the tubes 17 and 18 extend outwardly through side walls 19 so to form independent extensions for being easily attachable respectively to an irrigating fluid bottle to atmosphere (the bottle is not shown in the drawing), while the tube 11 is connected to a vacuum pump (also not shown). Both opposite ends of tubes 17 and 18 are accordingly open, as illustrated.

In use, as shown in FIG. 2, and as indicated by arrows 20, 21, and 22 thereof, infusion or irrigating liquid flows down into the stomach via infusion tube 17, atmosphere air flows down sump tube 18 into the closed lower end of tube 11, as irrigated substances are moved upward, via tube 11. The air from tube 18 aids in removing clots for obstructing holes 16.

In FIG. 5, a modified design 23 of the invention provides for tubes 17 and 18 to wind spirally within tube 11 in order to structurally reinforce tube 11 against collapsing.

Thus a modified design is provided.

While various changes may be made in the detail construction, it is understood that such changes will be within the spirit and scope of the present invention as is defined by the appended claims.

What is claimed is:

1. A nasogastric tube assembly comprising a flexible irrigation tube in combination with spaced smaller diameter infusion and sump tubes mounted longitudinally on the inner surface of said irrigation tube, wherein said irrigation tube includes an imperforate inner end wall and perforations spaced from said end wall, said sump tube being connected to an air supply and having an end orifice at a predetermined distance from said irrigation tube end wall, said irrigation tube being connected to vacuum producing means at its outer end, wherein said infusion tube is connected at its outer end to liquid irrigation means and having inner terminal outlet extending through and beyond said end wall a distance sufficiently spaced from said perforations whereby the irrigation liquid issuing from said outlet is not immediately sucked back into the irrigation and whereby said irrigation liquid functions to properly irrigate and dilute stomach contents before being suctioned out via the irrigation tube said tube assembly further including means for internally reinforcing the irrigation tube against radial collapse wherein said means are provided by said tubes, wherein said means comprises portions of said infusion and sump tubes are spirally coiled and in supporting abuttment with the irrigation tube.

* * * * *